United States Patent
Sang et al.

(10) Patent No.: US 10,421,704 B2
(45) Date of Patent: Sep. 24, 2019

(54) PROCESS FOR PD-CATALYZED HYDROXYCARBONYLATION OF DIISOBUTENE: RATIO OF 3,5,5-TRIMETHYLHEXANOIC ACID/H₂O

(71) Applicant: EVONIK DEGUSSA GMBH, Essen (DE)

(72) Inventors: Rui Sang, Liaocheng (CN); Peter Kucmierczyk, Herne (DE); Kaiwu Dong, Bo Zhou (CN); Ralf Jackstell, Rostock (DE); Matthias Beller, Ostseebad Nienhagen (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 16/188,995

(22) Filed: Nov. 13, 2018

(65) Prior Publication Data

US 2019/0194108 A1 Jun. 27, 2019

(30) Foreign Application Priority Data

Dec. 21, 2017 (EP) .................................. 17209295

(51) Int. Cl.
| | |
|---|---|
| *C07C 51/14* | (2006.01) |
| *B01J 31/00* | (2006.01) |
| *B01J 31/22* | (2006.01) |
| *B01J 31/30* | (2006.01) |
| *B01J 31/24* | (2006.01) |
| *C07C 53/128* | (2006.01) |

(52) U.S. Cl.
CPC ............ *C07C 51/14* (2013.01); *B01J 31/2234* (2013.01); *B01J 31/2295* (2013.01); *B01J 31/2409* (2013.01); *B01J 31/30* (2013.01); *B01J 2231/321* (2013.01); *B01J 2531/842* (2013.01); *C07C 53/128* (2013.01)

(58) Field of Classification Search
CPC .. C07C 51/14; C07C 53/128; B01J 2231/321; B01J 31/2234
See application file for complete search history.

(56) References Cited

U.S. PATENT DOCUMENTS 7,138,544 B2 11/2006 Springer et al.

FOREIGN PATENT DOCUMENTS

EP 1657230 A1 5/2006

OTHER PUBLICATIONS

European Search Report dated Jun. 16, 2018 in EP 17 20 9295 (6 pages).
Brennführer, A. et al., Palladium-Catalyzed Carbonylation Reactions of Alkenes and Alkynes. ChemCatChem. vol. 1. 2009. pp. 28-41.
U.S. Appl. No. 16/189,029, filed Nov. 13, 2018, Sang et al.
U.S. Appl. No. 16/215,991, filed Dec. 11, 2018, Sang et al.
U.S. Appl. No. 16/216,004, filed Dec. 11, 2018, Sang et al.
U.S. Appl. No. 16/216,020, filed Dec. 11, 2018, Sang et al.
U.S. Appl. No. 16/216,037, filed Dec. 11, 2018, Sang et al.
U.S. Appl. No. 16/216,053, filed Dec. 11, 2018, Sang et al.

*Primary Examiner* — Sikarl A Witherspoon
(74) *Attorney, Agent, or Firm* — Smith, Gambrell & Russell, LLP

(57) ABSTRACT

Process for Pd-catalyzed hydroxycarbonylation of diisobutene: ratio of 3,5,5-trimethylhexanoic acid/H₂O.

6 Claims, No Drawings

PROCESS FOR PD-CATALYZED HYDROXYCARBONYLATION OF DIISOBUTENE: RATIO OF 3,5,5-TRIMETHYLHEXANOIC ACID/H₂O

The invention relates to a process for Pd-catalyzed hydroxycarbonylation of diisobutene: ratio of 3,5,5-trimethylhexanoic acid/H₂O Carboxylic acids including propionic acid, adipic acid and fatty acids are used in the preparation of polymers, pharmaceuticals, solvents and food additives. The routes leading to carboxylic acids generally include the oxidation of hydrocarbons, alcohols or aldehydes, the oxidative cleavage of olefins by ozonolysis, the hydrolysis of triglycerides, nitriles, esters or amides, the carboxylation of Grignard or organolithium reagents, and the halogenation and subsequent hydrolysis of methyl ketones in the haloform reaction.

The hydroxycarboxylation of olefins is a highly promising and environmentally-friendly method for obtaining carboxylic acids. Acetic acid is produced by carbonylation of methanol, which is carried out with iodide. In the Koch reaction, the addition of water and carbon monoxide to alkenes is catalyzed by strong bases. This method is effective with alkenes that form secondary and tertiary carbocations, e.g. isobutylene to pivalic acid. Hydroxycarboxylation occurring with the simultaneous addition of CO and H₂O to alkenes/alkynes provides a direct and convenient method for synthesizing carboxylic acids.

The object of the invention was to provide a process affording good conversion in the Pd-catalyzed hydroxycarbonylation of diisobutene (DIBN).

The object is achieved by the process as follows.

Process comprising the process steps of:
a) addition of diisobutene,
b) addition of a compound comprising Pd, wherein the Pd is capable of forming a complex,
c) addition of the ligand L1:

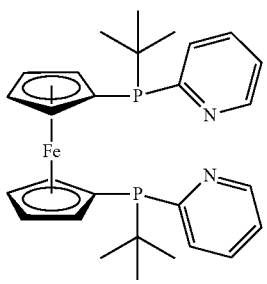

L1 d) addition of 3,5,5-trimethylhexanoic acid and water, wherein the ratio based on the volumes used is in the range from 0.75/1.25 to 1.8/0.2,
e) feeding in CO,
f) heating the reaction mixture such that the diisobutene is converted to the compound P1:

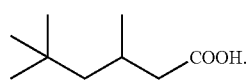

(P1)

In one variant of the process, the compound in process step b) is selected from: PdCl₂, PdBr₂, Pd(acac)₂, Pd(dba)₂ (dba=dibenzylideneacetone), PdCl₂(CH₃CN)₂.

In one variant of the process, the compound in process step b) is Pd(acac)₂.

In one variant of the process, the process comprises the additional reaction step g):
g) addition of CF₃SO₃H.

In one variant of the process, the reaction mixture is heated to a temperature in the range from 80° C. to 160° C. in process step f), preferably to a temperature in the range from 100° C. to 140° C.

In one variant of the process, the CO is fed in in process step e) such that the reaction proceeds under a CO pressure in the range from 20 bar to 60 bar, preferably in the range from 30 bar to 50 bar.

In one variant of the process, the ratio of 3,5,5-trimethylhexanoic acid/water based on the volumes used is in the range from 1.0/1.0 to 1.8/0.2.

In one variant of the process, the amount of 3,5,5-trimethylhexanoic acid added per 1 mmol of diisobutene is in the range from 0.3 ml to 0.4 ml.

The invention is elucidated in more detail by means of working examples below.

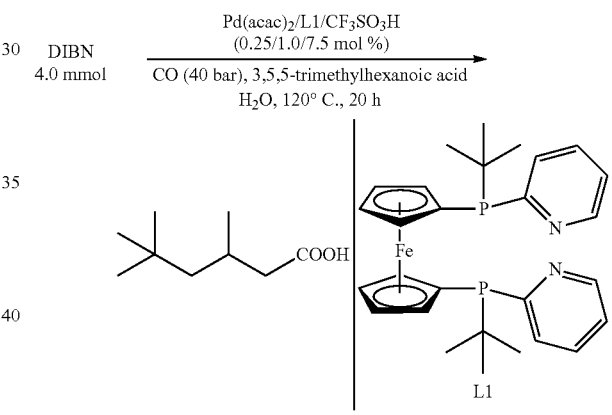

A 4 mL vial was charged with [Pd(acac)₂] (3.05 mg, 0.25 mol %), L1 (20.64 mg, 1.0 mol %) and oven dried stirring bar. The vial was then sealed with septa (PTFE-coated styrene-butadiene rubber) and a phenol resin cap. The vial was evacuated and refilled with argon three times. H₂O (0.5 ml), 3,5,5-trimethylhexanoic acid (1.5 ml), diisobutene (DIBN) (4.0 mmol) and CF₃SO₃

(7.5 mol %) were added to the vial by syringe. The vial was placed in an alloy plate, which was transferred to an autoclave (300 ml) of the 4560 series from Parr Instruments under argon atmosphere. After flushing the autoclave three times with CO, the pressure of CO was increased to 40 bar at room temperature. The reaction was conducted at 120° C. for 20 h. On conclusion of the reaction, the autoclave was cooled down to room temperature and cautiously decompressed. Isooctane (100 µl) was then added as internal standard. Conversion was measured by GC analysis.

The experiment described above was repeated with variation of the ratio of 3,5,5-trimethylhexanoic acid/water. All other parameters were maintained.

The results are compiled in the following table.

| Entry | 3,5,5-Trimethylhexanoic acid/water (mL/mL) | Conversion (%) |
|---|---|---|
| 1 | 0/2 | 25 |
| 2 | 0.2/1.8 | 45 |
| 3 | 0.5/1.5 | 49 |
| 4 | 1.0/1.0 | 84 |
| 5 | 1.50/0.5 | 87 |
| 6 | 1.8/0.2 | 72 |

The invention claimed is:

1. A process comprising:
a) adding diisobutene to form a reaction mixture,
b) adding a compound comprising Pd, wherein the Pd is capable of forming a complex to the mixture,
c) adding to the mixture ligand L1:

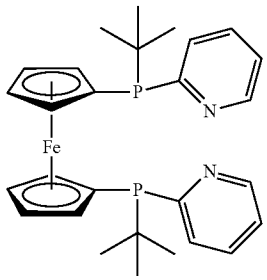

d) adding to the mixture 3,5,5-trimethylhexanoic acid and water, wherein the ratio based on the volumes used is in the range from 1.0/1.0 to 1.8/0.2,
e) feeding CO into the mixture,
f) heating the reaction mixture such that the diisobutene is converted to the compound P1:

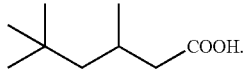

2. The process according to claim 1, wherein the compound in process step b) is selected from: $PdCl_2$, $PdBr_2$, $Pd(acac)_2$, $Pd(dba)_2$ (dba=dibenzylideneacetone) or $PdCl_2(CH_3CN)_2$.

3. The process according to claim 1, wherein the process further comprises
g) adding $CF_3SO_3H$.

4. The process according to claim 1, wherein the reaction mixture is heated to a temperature in the range from 80° C. to 160° C. in process step f).

5. The process according to claim 1, wherein the CO is fed in in process step e) such that the reaction proceeds under a CO pressure in the range from 20 bar to 60 bar.

6. The process according to claim 1, wherein the amount of 3,5,5-trimethylhexanoic acid added per 1 mmol of diisobutene is in the range from 0.3 ml to 0.4 ml.

* * * * *